US008777870B2

(12) United States Patent
Malek

(10) Patent No.: US 8,777,870 B2
(45) Date of Patent: Jul. 15, 2014

(54) FUNCTIONAL DISCOGRAPHY CATHETER

(76) Inventor: Michel H. Malek, Chicago, IL (US)

(*) Notice: Subject to any disclaimer, the term of this patent is extended or adjusted under 35 U.S.C. 154(b) by 921 days.

(21) Appl. No.: 12/120,846

(22) Filed: May 15, 2008

(65) Prior Publication Data

US 2009/0287118 A1  Nov. 19, 2009

(51) Int. Cl.
*A61B 5/00* (2006.01)
*A61B 5/103* (2006.01)
*A61B 5/117* (2006.01)
*A61M 31/00* (2006.01)

(52) U.S. Cl.
USPC ............ 600/561; 600/594; 604/508; 604/509

(58) Field of Classification Search
CPC ................ A61B 5/032; A61B 5/4566; A61B 2018/00339
USPC .................... 600/561, 594; 604/67, 508–510, 604/526–528; 73/1.66–1.69, 706
See application file for complete search history.

(56) References Cited

U.S. PATENT DOCUMENTS

| | | | | |
|---|---|---|---|---|
| 5,275,169 A | * | 1/1994 | Afromowitz et al. | 600/486 |
| 5,573,007 A | * | 11/1996 | Bobo, Sr. | 600/561 |
| 2002/0072679 A1 | * | 6/2002 | Schock et al. | 600/486 |
| 2004/0039371 A1 | * | 2/2004 | Tockman et al. | 604/528 |
| 2005/0234425 A1 | | 10/2005 | Miller et al. | |
| 2006/0224223 A1 | | 10/2006 | Podhajsky et al. | |
| 2006/0271088 A1 | * | 11/2006 | Alfrhan | 606/192 |
| 2007/0112299 A1 | | 5/2007 | Smit et al. | |
| 2009/0036799 A1 | * | 2/2009 | Sandhu et al. | 600/587 |

OTHER PUBLICATIONS

Lee, S. et al., "In vitro measurement of pressure in intervertebral discs and annulus fibrosus with and without annular tears during discography," Abstract printed from http://www.sciencedirect.com/science, on Jul. 14, 2008, pp. 1-3.
Mummaneni, P. V. et al., "Discogenic Low Back Pain," printed from http://www.spineuniverse.com/displayarticle.php/article3342.html, on Jul. 14, 2008, pp. 1-3.
Gunnar, B. J. et al., "The Sitting Posture: An Electromyographic and Discometric Study," *Orthopedic Clinics of North America*, Symposium on the Lumbar Spine, vol. 6, No. 1, Jan. 1975, pp. 105-120.
Shin, D.-A. et al., "Diagnostic Relevance of Pressure-Controlled Discography," *J. Korean Med. Sci.*, vol. 21, pp. 911-916 (2006).

* cited by examiner

*Primary Examiner* — Brian Szmal
*Assistant Examiner* — Megan Leedy
(74) *Attorney, Agent, or Firm* — Foley & Lardner LLP

(57) ABSTRACT

Catheter devices for diagnosing and treating discogenic pain are provided. The catheter devices comprise a tubular body configured for insertion into an intervertebral disc and a pressure measuring device disposed along the length of the tubular body, the pressure measuring device configured to measure the pressure within the intervertebral disc. The catheter devices are capable of measuring the pressure within an intervertebral disc of a subject while the subject is moving.

10 Claims, 2 Drawing Sheets

FUNCTIONAL DISCOGRAPHY CATHETER

FIELD OF THE INVENTION

The invention generally relates to catheter devices for the spine. More specifically, catheter devices are disclosed which are capable of measuring the pressure within an intervertebral disc of a subject while the subject is moving.

BACKGROUND

Discogenic pain is a form of back pain arising from one or more intervertebral discs in the spine. Discogenic pain occurs when there is a structural abnormality in an intervertebral disc, such as degeneration, a tear or herniation. In disc degeneration, fluid from the outer fibrous annulus surrounding an intervertebral disc is lost, causing the disc to become brittle. When the disc becomes so brittle that it cracks, the disc releases chemicals that may be a source of discogenic pain. Discogenic pain is also associated with activities that increase the pressure within the intervertebral disc, i.e., the intradiscal pressure. Sitting, bending forward, coughing and sneezing can increase the intradiscal pressure and lead to discogenic pain. In some cases, disc degeneration is chronic, resulting in a condition known as Degenerative Disc Disease.

To diagnose and treat discogenic pain, it is important to accurately locate the source of pain. Currently, discography is the most common way of diagnosing discogenic pain. During discography, a needle is inserted into an intervertebral disc suspected of causing the back pain and a contrast medium is injected into the disc through the needle. Using fluoroscopy, the physician can determine whether the contrast medium is properly positioned within the nucleus of the disc to get an idea about the health of the disc. If the disc is healthy, the contrast medium will stay in the nucleus. If the disc is damaged or degenerated, the contrast medium can spread easily throughout the disc. If the disc is ruptured, the contrast medium can actually discharge out of the nucleus. In addition, the injection of the contrast medium into the disc may cause pain, due to the chemical composition of the contrast medium and/or the increased pressure in the disc upon injection. During the procedure, the patient may be asked to respond if any pain is experienced, especially pain that mimics the condition that the patient is complaining of. Through a combination of subjective analysis of radiographs and a subjective description of the pain reported by the patient, the physician attempts to determine whether the particular disc is causing the patient's pain. In this type of discography procedure, the patient generally remains immobilized.

Despite the widespread use of discography, there are some drawbacks. Some clinicians theorize that if a discogram is positive according to commonly used criteria, then the tested disc is the source of the patient's pain. However, there is no universally accepted definition of the criteria for a positive discogram. As a result, interpretation of discograms is somewhat controversial. Not only does the test rely on subjective feedback, but results themselves have been shown to have a high rate of false positives and false negatives, with a significant number of patients with no back pain having positive discograms. Similarly, some patients have reported feeling a replication of their usual pain during discography, even though it is later found that another, non-discogenic cause was the actual origin of the pain. Moreover, discography is not a particularly selective technique in that it cannot necessarily target a particular portion of the intervertebral disc that is damaged and causing a subject's pain.

In another method of diagnosing and treating discogenic pain, a catheter is inserted into an intervertebral disc. The subject may assume a position that causes the discogenic pain and an anesthetic or analgesic is injected into the disc. The patient is then asked to report whether or not the injected substance has allieviated the pain. However, like the conventional disography procedure described above, this method relies on subjective feedback and is not particularly selective. In addition, this method provides only limited data, i.e., the presence or absence of pain.

SUMMARY

Catheter devices for diagnosing discogenic pain and methods for using the devices are provided herein. The catheter devices are capable of measuring the pressure within an intervertebral disc of a subject while the subject is moving, including while the subject is engaging in and/or undergoing a motion that causes and/or reproduces the subject's discogenic pain. By itself, the pressure measurement obtained while the subject is moving provides objective data closely related to the actual conditions that cause the subject's pain. Thus, the pressure measurement is especially useful in accurately diagnosing and treating discogenic pain. The catheter devices may also be designed to be steerable so as to target specific portions of an intervertebral disc, thereby providing an even more accurate diagnosis.

The catheter devices comprise a tubular body configured for insertion into an intervertebral disc of a spinal column. The tubular body comprises at least one lumen for providing passage through the tubular body. The lumen may be configured to serve a variety of purposes. The size, shape, and materials used to form the tubular body may vary. In addition, the tubular body may comprise one or more features that facilitate insertion of the catheter device into the intervertebral disc or visualization of the catheter device inside the subject. In some aspects, the tubular body further comprises a steering member configured to steer the catheter device to specific portions of the intervertebral disc. A variety of steering members may be used.

The catheter devices further comprise a pressure measuring device disposed along the length of the tubular body. The pressure measuring devices, which are capable of measuring intradiscal pressure, may comprise one or more pressure sensors. A variety of pressure sensors may be used. In some aspects, the pressure measuring device comprises an expandable member coupled to the distal portion of the tubular body and a pressure sensor configured to measure the pressure within the expandable member. In some such aspects, the expandable member is an inflatable balloon. The size, shape, and materials used to form the inflatable balloon may vary.

The catheter devices may further comprise one or more anchors coupled to the tubular body and configured to maintain the position of the catheter device within the intervertebral disc. The type of anchor, location of the anchor along the tubular body, and means of attachment of the anchor to the tubular body may vary. In some aspects, the anchor comprises an expandable member coupled to the distal portion of the tubular body. In another aspect, the anchor comprises an attachment member configured to attach to an intervertebral disc. A variety of attachment members may be used. The size and materials used to form the anchors and attachment members may vary.

The catheter devices may further comprise other components. In some aspects, the catheter devices comprise components ancillary to the pressure measuring devices. In other aspects, the catheter devices comprise a guidewire coupled to the tubular body and configured to guide the catheter device into an intervertebral disc.

Various therapeutic agents may be used with the catheter devices disclosed herein. Therapeutic agents include a wide variety of substances capable of alleviating or treating discogenic pain. Therapeutic agents include diagnostic agents and agents useful for the repair of the components of an intervertebral disc. In some aspects, the therapeutic agent may be administered through a lumen of the tubular body. In other aspects, the therapeutic agent is coated onto or impregnated into one or more components of the catheter device.

Also disclosed herein are methods of using the catheter devices. The methods involve inserting into an intervertebral disc of a subject any of the catheter devices disclosed herein. Techniques for inserting catheter devices into intervertebral discs are known. The methods further comprise measuring the pressure within the intervertebral disc. In some aspects, the intradiscal pressure is measured while the subject is moving, including while the subject engages in movements that reproduce the subject's discogenic pain.

The methods of using the catheter devices disclosed herein may be combined with other types of discography, including the discography procedures described above. Thus, the pressure measurements obtained by using the disclosed catheter devices may be correlated with other data, including, but not limited to, dye-based discograms and pain measurements before and/or after administration of a therapeutic agent to the subject. As such, the devices and methods disclosed herein allow a more accurate, comprehensive analysis of discogenic pain over other diagnostic techniques. By way of a non-limiting example, one method involves inserting the appropriate, steerable catheter device into a portion of an intervertebral disc of a subject, performing dye-based discography, measuring the intradiscal pressure while the subject is moving, administering an anesthetic to the subject, and measuring the subject's pain level before and after administration of the anesthetic. Such a method may be known as selective functional anesthetic discometric discography and the associated catheter device may be known as a selective functional anesthetic discometric discography catheter device.

DETAILED DESCRIPTION

Figure 1:
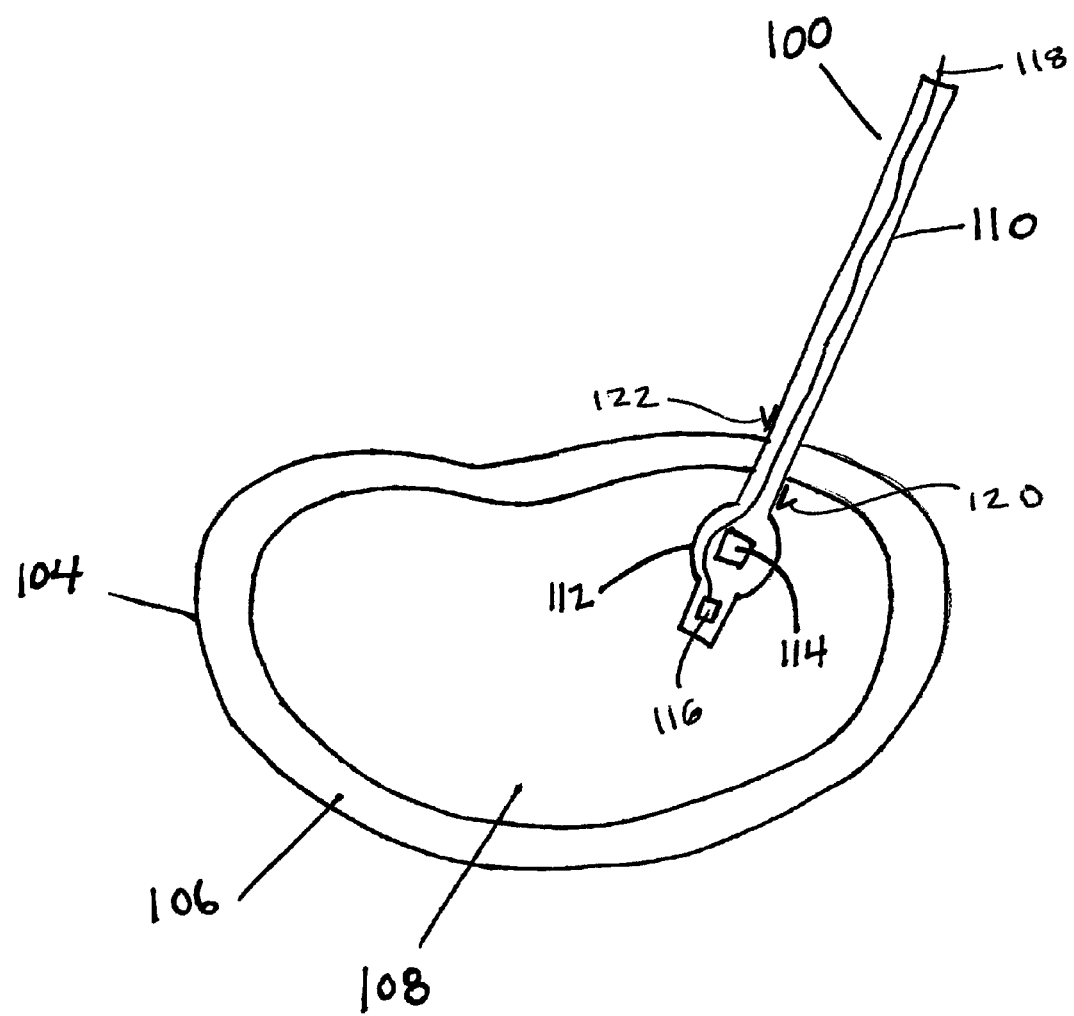
FIG. 1 shows a catheter device inserted into an intervertebral disc.

Catheter devices for diagnosing discogenic pain and methods for using the devices are provided herein. The catheter devices disclosed herein comprise a tubular body configured for insertion into an intervertebral disc of a spinal column. The tubular body has a proximal portion, a shaft, and a distal portion, the distal portion contacts the intervertebral disc. The dimensions of the tubular body may vary, provided it is capable of being inserted into an intervertebral disc. The dimensions may be chosen to minimize interference with other components of the spinal column. Similarly, the exact shape of the tubular body may vary. In some aspects, the tubular body may form an approximately straight line from one end of the body to the opposite end of the body. In other aspects, the tubular body may be curved. In further aspects, portions of the tubular body may be straight, while other portions may be curved. In still other aspects, the proximal portion, the distal portion, or both portions of the body may be curved. In other aspects, one or both ends of the tubular body may be bifurcated.

The tubular body may be constructed from a variety of materials, including, but not limited to, a metal, a polymer, or combinations thereof. Suitable metals include, but are not limited to, stainless steel, titanium, platinum, tantalum, gold and their alloys; gold-plated ferrous alloys; platinum-plated titanium, stainless steel, tantalum, gold and their alloys as well as other ferrous alloys; cobalt-chromium alloys; and titanium nitride-coated stainless steel, titanium, platinum, tantalum, gold, and their alloys. Suitable polymers include, but are not limited to, acrylonitrile polymers such as acrylonitrile-butadiene-styrene polymer, and the like; halogenated polymers such as polytetrafluoroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and combinations thereof. Other materials that may be used to form the tubular body include those disclosed in U.S. Patent Publication No. 2005/0234425.

Depending upon the materials used to form the tubular body, the body may be rigid or flexible. In addition, some portions of the tubular body may be flexible while other portions may be rigid. In some aspects, proximal portion, the distal portion, or both portions of the tubular body are flexible.

The tubular body comprises at least one lumen for providing passage through the tubular body. The one or more lumens may be configured to serve a variety of purposes. In some aspects, a lumen may be configured for insertion and/or expansion of an expandable member. In other aspects, a lumen may be configured for administration of one or more therapeutic agents to the intervertebral disc. In yet further aspects, a lumen may be configured for insertion of a guidewire, a pressure sensor, an endoscopic scope, or other similar device. Endoscopic scopes enable the visualization of the intervertebral disc. Expandable members, therapeutic agents, guidewires, and pressure sensors are further described below.

In some aspects, the tubular body comprises a single lumen. In other aspects, the tubular body comprises two separate lumens, or more than two separate lumens. Each lumen may be configured to serve any of the purposes described above or combinations of such purposes. By way of non-limiting examples only, in some aspects, the tubular body comprises a single lumen configured for insertion and/or expansion of an expandable member. In another aspect, the tubular body comprises two lumens, one configured for insertion of a pressure sensor and the other configured for insertion of a guidewire. In yet another aspect, the tubular body comprises two lumens, one configured for insertion of a guidewire and/or a pressure sensor, and the other configured for administration of one or more therapeutic agents.

In those aspects including multiple lumens, the configuration of the lumens within the tubular body may vary. In some aspects, at least a portion of the lumens are coaxial. In such aspects, the diameter of the first lumen is large enough so that the second lumen may fit within the first lumen. In other aspects, at least a portion of the lumens are positioned in a side-by-side arrangement.

The tubular body may comprise one or more features that facilitate insertion of the catheter device into the intervertebral disc. In some aspects, the distal portion of the tubular body is tapered, pointed, or both to facilitate the passage of the tubular body through one or more components of the intervertebral disc, e.g., the annulus fibrosis. In other aspects, the tubular body may comprise a removable or non-removable pointed stylet coupled to the distal portion of the tubular body. Other possible features are disclosed in U.S. Patent Publication No. 2005/0234425.

In another aspect, the tubular body may further comprise a steering member configured to steer the catheter device to specific portions of the intervertebral disc. This feature may be useful for cases in which select portions of the disc may be damaged, making it desirable to pinpoint those areas of the disc for treatment. In some aspects, the steering member comprises a wire or rod or similar component embedded into a wall of the tubular body and extending along the length of the tubular body, from one end to the other end. The steering member may extend beyond the proximal end of the tubular body and may be movable by a user. In such aspects, the distal portion of the tubular body may be flexible so that when the steering member is moved at the proximal end of the tubular body, the distal portion of the tubular body also moves. The dimensions and materials used to form the steering member may vary. In some aspects, the materials used to form the steering member include any of the polymers and metals disclosed herein, or combinations thereof.

The tubular body may further comprise one or more features that facilitate visualization of the catheter device inside a subject and/or features that indicate the depth of insertion inside the subject. In some aspects, the tubular body comprises one or more markings disposed along the shaft of the tubular body. A variety of markers may be used, including lines, colors, or radiopaque materials. Other suitable markers are disclosed in U.S. Patent Publication No. 2005/0234425.

The catheter devices disclosed herein further comprise a pressure measuring device disposed along the length of the tubular body. The pressure measuring devices are capable of measuring the pressure within an intervertebral disc, i.e., the intradiscal pressure. The pressure measuring devices may further be capable of converting the pressure measurement into an appropriate signal, e.g., an electrical signal, and transmitting the pressure measurement to a display.

The pressure measuring devices may comprise one or more pressure sensors. A variety of pressure sensors may be used including, but not limited to, a strain gauge sensor, an optical strain sensor, a fiber optic sensor, an electromechanical sensor, or an electromechanical sensor array such as a micro-electromechanical system (MEMS). In some aspects, as shown in FIG. 1, the pressure measuring device comprises a fiber optic sensor 116 coupled to the distal portion of the tubular body 110. In some aspects, the fiber optic sensor 116 is attached to the tubular body 110 through any suitable means. In other aspects, the fiber optic sensor 116 is attached to a cable or wire, e.g., a fiber optic cable 118, that may be inserted through a lumen of the tubular body 110.

In other aspects, the pressure measuring device comprises an expandable member coupled to the distal portion of the tubular body. By expandable member, it is meant any structure that increases in size laterally from the catheter device. In such aspects, the pressure measuring device further comprises a pressure sensor coupled to the expandable member for measuring the pressure within the expandable member. The expandable member may be attached to the tubular body through any suitable means. By way of example only, the expandable member may be attached to the tubular member by adhesives, friction fitting, snap fitting, screw fitting, or the like. Similarly, the pressure sensor may be attached to the expandable member by any suitable means. In other aspects, the pressure sensor may be attached to a cable or wire and inserted through a lumen of the tubular body and into the expandable member. In yet other aspects, the pressure sensor need not be physically attached to the expandable member at all, provided that it is capable of measuring the pressure within the expandable member.

In some aspects, the expandable member is an inflatable balloon. The catheter device is inserted into the intervertebral disc of an immobilized subject and the balloon is inflated within the intervertebral disc using a fluid, e.g., a gas or a liquid. The fluid within the inflated balloon will be characterized by a particular pressure. When the subject is allowed to move, the motion of the spine may cause the pressure of the fluid inside the inflated balloon to change. The pressure change of the fluid within the inflated balloon is indicative of the change in intradiscal pressure that accompanies motion of the subject's spine. Thus, in this aspect of the invention, the pressure measuring device indirectly measures the pressure in the intervertebral disc by measuring the pressure of the fluid in the inflated balloon within the intervertebral disc.

The dimensions and materials used to construct the inflatable balloon may vary. The exact size and shape of the inflatable balloon are not critical. In general, the balloon is sized so that it fits within the intervertebral disc space upon inflation. The balloon may take the form of a sphere, cylinder, or any other shape. The balloon may comprise a variety of materials, including, but not limited to polymers. Suitable polymers include, but are not limited to polyethylene terephthalates, polyolefins, polyurethanes, nylon, polyvinyl chloride, silicone, polyetherketone, polylactide, polyglycolide, poly(lactide-co-glycolide), poly(dioxanone), poly([epsilon]-caprolactone), poly(hydroxylbutyrate), poly(hydroxylvalerate), tyrosine-based polycarbonate, polypropylene fumarate, and mixtures and combinations thereof. Other suitable balloons are disclosed in U.S. Patent Application Publication No. 2006/0247567.

In other aspects, the pressure measuring device comprises two or more sensors. In some such aspects, there are two pressure sensors. A first pressure sensor may be coupled to the distal portion of the tubular body for measuring the intradiscal pressure at one location within the disc. A second pressure sensor may be coupled to the distal portion of the tubular body for measuring the intradiscal pressure at a different location within the same disc or the intradiscal pressure in a different disc. In another embodiment, a first pressure sensor may be coupled to the distal portion of the tubular body for measuring the intradiscal pressure. A second pressure sensor may be coupled to the proximal portion of the tubular body for measuring the pressure outside of the intervertebral disc. Thus, in this aspect, the pressure measuring device may be configured to provide the differential pressure across the intervertebral disc. In yet a further aspect, a first pressure sensor may be associated with an expandable member and configured to measure the pressure within the expandable member as described above. A second pressure sensor may also be coupled to the distal portion of the tubular body for directly measuring the intradiscal pressure. In some aspects, the second pressure sensor may be a fiber optic sensor.

The catheter devices disclosed herein may further comprise other components ancillary to the pressure measuring devices. By way of example only, the catheter devices may comprise components for providing a source of power or a source of light to the pressure sensor; circuitry or electronics for detecting the output of the pressure sensor; and/or components for displaying, recording, and storing output of the pressure sensors.

The catheter devices disclosed herein may further comprise one or more anchors disposed along the length of the tubular body, as shown in FIG. 1, and configured to maintain the position of the catheter device within the intervertebral disc. The position of the anchor along the tubular body may vary. In some aspects, the anchor is positioned along the distal portion of the tubular member. In other aspects, the anchor is positioned along the tubular body so that upon insertion of the catheter device into the subject, the anchor ends up inside the intervertebral disc. In yet other aspects, the anchor is positioned along the tubular body so that upon insertion of the catheter device into the subject, the anchor remains outside of the disc. In still other aspects, the catheter devices comprise two anchors 120, 122, each positioned so that upon insertion of the catheter device into the subject, one anchor (120) is inside the intervertebral disc and the other (122) is outside of the disc. The use of two anchors may further ensure that the catheter device remains in position and at the correct depth within the disc. The anchor may be attached to the tubular body in a variety of ways. By way of example only, the anchor may be attached to the tubular body by adhesives, friction fitting, snap fitting, screw fitting, or the like.

A variety of anchors are suitable for use with the catheter devices disclosed herein. In some aspects, the anchor comprises an expandable member coupled to the distal portion of the tubular body. In such aspects, the catheter device, along with the expandable member, may be inserted into the intervertebral disc. Once the expandable member is inside the intervertebral disc, anchoring is achieved by expanding the member to prevent the catheter device from being pulled back through the disc. In some aspects, the expandable member is an inflatable balloon. However, a variety of other expandable members may be suitable, including, but not limited to those disclosed in U.S. Patent Publication 2005/0234425.

In other aspects, the anchor comprises an attachment member configured to attach to an intervertebral disc. Suitable attachment members include, but are not limited to, screws, hooks, barbs, T-tags, or the like. The attachment member may attach to various components of an intervertebral disc, including, but not limited to the annulus fibrosis. In yet further aspects, the anchor is formed by including threads on the surface of the tubular body itself. In such aspects, the tubular body may be anchored by screwing into the intervertebral disc. Other anchors include, but are not limited to those disclosed in U.S. Patent Publication 2005/0234425.

The dimensions of the anchors and the materials used to form the anchors may vary. The exact size and shape of the anchor is not critical, provided it is small enough to be implanted into a subject and large enough to function as an anchor. Any of the materials disclosed above may be used to form the anchors, expandable members, inflatable balloons, and attachment members. In some aspects, the expandable members may comprise polyvinyl chloride (PVC), Polyethylene, Polyether Block Amide (PEBAX), Polyethylene Terepthalate (PET), Polyester, Nylon, Polyurethanes, Polyether Block Amide (PEBAX), Polyolefins or any suitable combination thereof.

The catheter device may further comprise a guidewire coupled to the tubular body and configured to guide the catheter device into an intervertebral disc. In such an aspect, the guidewire may be inserted into the intervertebral disc prior to inserting the catheter, so that the guidewire provides a line over which the tubular member of the catheter can slide over and into the disc. The guidewire may remain in place or may be subsequently removed.

The dimensions of the guidewire and the materials used to form the guidewire may vary. The exact size and shape of the guidewire is not critical. The guidewire may be straight, curved, or may comprise portions that are straight and portions that are curved and/or bent. In some aspects, the end of the guidewire is capable of assuming a bent, spiral, or zig-zag shape after it is inserted into the intervertebral disc. This feature may be useful for maintaining the position of the guidewire within the disc. Any of the materials disclosed above may be used to form the guidewire. Exemplary materials include, but are not limited to, stainless steel and shape-memory materials such as Nitinol, spring stainless steel or the like.

Any therapeutic agent capable of alleviating or treating discogenic pain can be used in the catheter device of the present invention. In some aspects, the therapeutic agent is administered through a lumen of the tubular body. In other aspects, the therapeutic agent is coated onto or impregnated into one or more components of the catheter device. The therapeutic agent can be an anesthetic, an analgesic, an antibiotic, a hydrating agent, a supportive agent, a prolotherapy agent, collagen, a stem cell, Osteogenic Protein-1, ethanol, alcohol, a steroid, a dye, a radio-opaque contrast agent, an ultrasound contrast agent, Bone Morphogenetic Protein (BMP), a Serotonin 5-HT2A receptor inhibitor, LMP-1, TIMP-1, TGF-1, TGF-2, Rofecoxib, Ketorolac, Glucosamine, Chondroitin Sulfate, Dextrose, DMSO, a non-steroidal antiinflammatory drug, ibuprofen, naprosyn, Bextra, Vioxx, Celebrex, indomethacin, botulinum toxin, capsaicin, a vanilloid agonist, vanilloid antagonists, VR1, VRL-1, methylprednisolone or chymopapain. Thus, a therapeutic agent includes a diagnostic agent such as a dye, a radio-opaque contrast agent, and the like. Similarly, a therapeutic agent also includes agents capable of repairing the various components of the intervertebral disc.

Examples of anesthetics and analgesics include lidocaine, chloroprocaine, mepivacaine, ropivacaine, xylocaine, prilocaine, morphine, bupivocaine, marcaine, 2-chloroprocain, fentanyl, diamorphine, meperidine, methadone, alfentanil, hydromorphone, lofentanil, sufentanil, buprenorphine, other opoids, adrenergic agonists, somatostatin analogs, calcium channel blockers, N-methyl-D-aspartate receptor antagonists, ketamine, benzodiazepines, kionidine, tizanidine, midazolam, levorphanol, heterocyclic antidepressants, nonheterocyclic, serotonin-enhancing antidepressants, GABA analogues, psychogenic amines, somatostatin, octreotide, SNX-111, midazolam, methylprednisolone acetate, Aristospan, ethyl chloride, etidocaine, linocaine, triamcinolone diacatate, Astramorph, Duramorph, Dilaudid, Sensorcaine MPF, Baclofen (Lioresal), Clonidine, baclofen, codeine, neurontin and Demerol. Examples of antibiotics include, but are not limited to, penicillins, cephalosporins, tetracycline, erythromycin, clindamycin, vancomycin, bacitracin, doxycycline, ampicillin, levaquin, metronidazole, azithromycin, ciprofloxacin, augmentin, bactrim, TMP-SMX, rocephin, gentamycin, keflex and macrobid.

Non-limiting examples of various therapeutic agents are included herein. Examples of hydrating agents include hypotonic saline, isotonic saline or hypertonic saline. Examples of supporting agents include a hydrogel, ethylene-vinyl alcohol copolymer, dimethyl sulfoxide or tantalum. Examples of prolotherapy agents include sodium morrhuate, cod oil, phenol, minerals or ethyl alcohol. Examples of Bone Morphogenetic Protein include BMP-2, BMP-4, BMP-6, BMP-7 and BMP-12. Other therapeutic agents are disclosed in U.S. Patent Publication 2005/0234425.

The catheter devices disclosed herein, and the associated components of the devices, may be configured to be left in the subject for extended periods of time. In general, this means that the devices and the associated components comprise a size, shape, and material that permits the device and its components to remain implanted in the subject without significant irritation to the subject or interference with the subject's activities. The period of time may vary. In some aspects, the catheter devices may remain implanted for hours, days, weeks, even months.

The figures show examples of catheter devices according various embodiments. The embodiments shown in the figures are intended only to exemplify the invention and should not be construed to limit the invention to any particular embodiment. The drawings are not necessarily to scale and the relative dimensions of the components of the apparatuses provided therein may deviate from those shown in the figures.

FIG. 1 illustrates a catheter device 100 inserted in an intervertebral disc 104. The intervertebral disc comprises components, the annulus fibrosis 106 and the nucleus pulposus 108. The catheter device comprises a tubular body 110 and an inflatable balloon 112 and a pressure sensor 114 at the distal end of the tubular body. In FIG. 1, the tubular body is straight with a blunt distal end. However, other tubular bodies may be used as described above. Similarly, the tubular body of FIG. 1 comprises a single lumen, but multiple lumens may be used. In FIG. 1, the balloon is inflated and the pressure sensor is located inside the balloon. However, as described above, the pressure sensor does not necessarily have to be located within the balloon or even directly attached to the balloon as long as it is capable of measuring the pressure of the fluid inside the balloon. In FIG. 1, the inflated balloon also serves as an anchor. However, other anchors may be used.

Figure 2A:
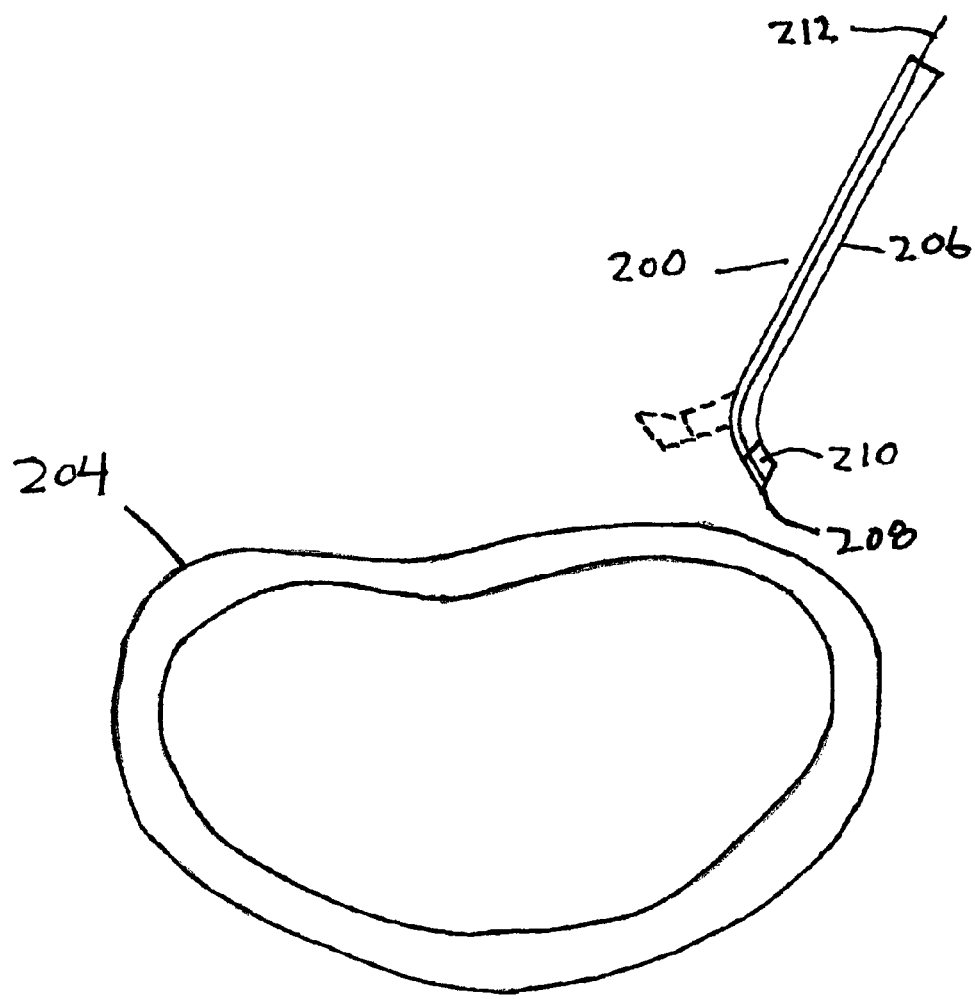
FIG. 2A shows a steerable catheter device prior to insertion into an intervertebral disc.
Figure 2B:
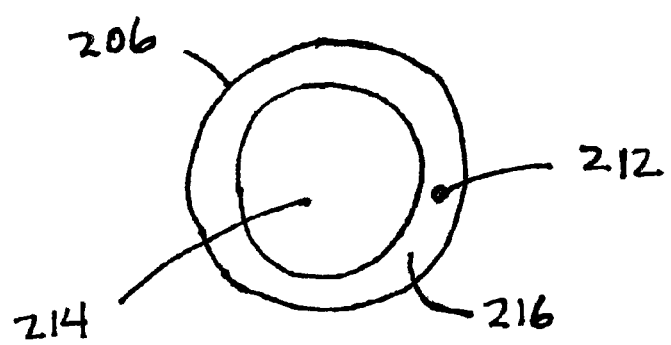
FIG. 2B shows a cross-section of the tubular body of the steerable catheter device.

FIG. 2A illustrates another catheter device 200. This catheter device is shown just prior to insertion into the intervertebral disc 204. The catheter device comprises a tubular body 206. The distal end 208 of the tubular body is pointed to facilitate insertion through the intervertebral disc. The catheter device also comprises a pressure sensor 210 coupled to the distal end of the tubular body for direct measurement of the intradiscal pressure upon insertion. In FIG. 2A, the tubular body comprises a steering member configured to steer the catheter device to specific portions of the intervertebral disc. The steering member comprises a wire 212 extending along the length of the tubular body, from the proximal end to the distal end. As described above, movement of the wire at the proximal end of the tubular body causes the distal end of the tubular body to move. The movement of the distal end of the tubular body is represented by dotted lines. This steerable catheter device allows the device to target a specific portion of the intervertebral disc. FIG. 2B shows a cross-section of the tubular body 206 and its lumen 214. The wire 212 is embedded within the wall 216 of the tubular body. Although FIGS. 2A and 2B show only one wire coupled to the tubular body, more wires may be used in order to provide additional control over the steering of the catheter device.

Also provided herein are methods of using any of the catheter devices described above. In a basic embodiment, the methods comprise inserting into an intervertebral disc of a subject any of the catheter devices disclosed herein. Techniques for inserting catheter devices into intervertebral discs are well-known. By way of example only, insertion of a catheter device may be accomplished as follows. The catheter device may be inserted into an intervertebral disc by way of an introducer device. An introducer device having a lumen is inserted into the back of a subject. The introducer is assisted by an obturator inserted through the lumen of the introducer. Once placed in proximity to the anterior portion of the spine and near an intervertebral disc, the obturator is removed and replaced by an injection needle. The injection needle is inserted into the annulus fibrosis to position its distal end in the nucleus pulposus. Confirmation that the needle is in the nucleus pulposus can be obtained using contrast dye or any other imaging means. Once confirmed that the needle is in the nucleus pulposus, a guidewire can be passed through the needle such that it also pierces into the nucleus pulposus. Subsequently, the tubular member of the catheter can be passed over the guidewire such that it enters the intervertebral disc. At this point, the introducer device, guidewire and the injection needle can be removed.

Alternatively, the catheter device can be inserted into an intervertebral disc without the assistance of a guidewire In this aspect, the tubular member is passed through an introducer device with a pointed stylet inserted through the lumen of the tubular member, protruding from the distal end. The stylet allows the catheter to be passed through the tough tissue of the annulus fibrosis. Subsequently, the stylet can be removed. Other methods for inserting the catheter device are disclosed in U.S. Patent Publication U.S. 2005/0234425. In yet further aspects, the catheter device may be inserted without the assistance of either a guidewire or an introducer device.

The methods further comprise measuring the pressure within the intervertebral disc. The pressure may be measured at various points in time. By way of example only, the pressure may be measured at a point when the subject is immobilized or after the subject has assumed a particular position. In other aspects, the pressure may be measured continuously. In some such aspects, the pressure may be measured while the subject is moving. In particular, the subject may engage in or undergo a motion that causes and/or reproduces the subject's discogenic pain. By itself, the pressure measurement obtained while the subject is moving provides objective data closely related to the actual conditions that cause the subject's pain. Thus, the pressure measurement is especially useful in accurately diagnosing and treating discogenic pain.

However, the pressure measurements may be correlated with other measurements. For example, while the subject is moving, the subject may be asked to indicate whether the subject feels pain. These subjective pain measurements may be correlated with the pressure measurements, thereby providing additional information from which to pinpoint the location and diagnosis of the damaged disc. Similarly, the pressure measurements may be correlated with the administration of therapeutic agents and/or with the results of dye-based discography, as further described below.

The methods may further comprise other steps. In some aspects, the methods comprise steering the catheter device to a specific portion of the intervertebral disc using any of the steering members disclosed above. In other aspects, the methods comprise anchoring the catheter device to the intervertebral disc using any of the anchors described above. In yet other aspects, the methods comprise administering a therapeutic agent to the intervertebral disc. In some such aspects, administration of the therapeutic agent involves introducing the therapeutic agent through the catheter device, i.e., through a lumen of the tubular body.

The methods may be combined with other conventional techniques used to diagnose discogenic pain. In some aspects, the methods further comprise performing dye-based discography on the subject, as described in the background section. In other aspects, the methods further comprise administering a therapeutic agent to the subject and measuring the subject's level of pain before and after administration of the therapeutic agent. Either of these techniques may be performed at any point in time, before or after the pressure measurement.

By way of another non-limiting example, one method involves inserting the appropriate catheter device into an intervertebral disc of a subject. The catheter device may be a steerable catheter device, as described above, which may be inserted into a specific portion of the intervertebral disc. Next, dye-based discography may be performed. Next, the subject may be asked to assume a position or engage in a motion that reproduces the subject's discogenic pain. The intradiscal pressure may be measured before, during, and after this activity. In addition, the pain experienced by the patient before, during, and after the activity may be recorded. Next, a therapeutic agent, e.g., an anesthetic, may be administered to the intervertebral disc. The subject may be asked to repeat the pain-producing activity. Again, the intradiscal pressure may be measured and the subject's pain response may be recorded before, during, and after the activity. The method described may be known as selective functional anesthetic discometric discography and the associated catheter device may be known as a selective functional anesthetic discography catheter device. Finally, because the catheter devices disclosed herein may be configured to remain within the subject for an extended period of time, the steps just described may take place over various periods of time and in various locations. For example, insertion of the catheter device and performance of dye-based discography may take place in one room of the clinic, hospital, or the like, and the subject may be moved to a different room or rooms for the other steps. Similarly, the subject may rest in between one or more of any of the steps described.

In yet another aspect, the method comprises measuring the intradiscal pressure over an extended period of time. As described above, the catheter devices disclosed herein may be configured to remain implanted in a subject for extended periods of time, including, but not limited to hours, days, weeks, or months. Such catheter devices may be used to monitor the subject's intradiscal pressure at various points during these extended periods of time. In some aspects, the catheter device is inserted into the subject's intervertebral disc and the intradiscal pressure may be measured as described above whenever the subject visits the hospital or clinic. In other aspects, the intradiscal pressure may be measured during the subject's normal, everyday activities outside of the hospital or clinical setting. For example, the catheter's pressuring measuring device may include a portable memory unit that may be coupled to the one or more pressure sensors. The subject's intradiscal pressure may be measured at various points in time, including during the subject's normal everyday activities, and the output saved to the memory unit. The measurements may be subsequently reviewed by the subject's physician.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

For the purposes of this disclosure and unless otherwise specified, "a" or "an" means "one or more." All patents, applications, references and publications cited herein are incorporated by reference in their entirety to the same extent as if they were individually incorporated by reference.

While some detailed embodiments have been illustrated and described, it should be understood that such detailed embodiments are merely exemplary and changes and modifications can be made therein in accordance with ordinary skill in the art without departing from the invention in its broader aspects as defined in the following claims.

The invention claimed is:

1. A catheter device comprising:
   a tubular body comprising at least one lumen, the tubular body configured for insertion into an intervertebral disc; and
   a first pressure measuring device disposed at a distal portion of the tubular body, the pressure measuring device configured to measure the pressure within the intervertebral disc,
   wherein the first pressure measuring device comprises an expandable member and a pressure sensor disposed on the expandable member and configured to measure the pressure within the expandable member in order to measure the pressure within the intervertebral disc;
   a second pressure measuring device comprising a fiber optic sensor coupled to the tubular body proximate the distal portion, and a fiber optic cable coupled to the fiber optic sensor and extending at least partially through one of the at least one lumen; and
   a first anchor attached to the tubular body and having a first attachment member configured for placement inside, and attachment to, the intervertebral disc and a second anchor attached to the tubular body and having a second attachment member configured for placement outside, and attachment to, the intervertebral disc.

2. The catheter device of claim 1, wherein the expandable member is configured to maintain the catheter device within the intervertebral disc.

3. The catheter device of claim 2, wherein the expandable member is an inflatable balloon and the pressure sensor is selected from the group consisting of a strain gauge sensor, an optical strain sensor, a fiber optic sensor, an electromechanical sensor and an electromechanical sensor array.

4. The catheter device of claim 1, the tubular body further comprising a steering member, the steering member configured to steer the catheter device to a portion of the intervertebral disc.

5. The catheter device of claim 4, wherein the steering member comprises a wire embedded within a wall of the tubular body and extending along the length of the tubular body.

6. The catheter device of claim 1, wherein a distal portion of the tubular body is flexible.

7. The catheter device of claim 1, wherein the catheter device is impregnated with or coated with a therapeutic agent.

8. The catheter device of claim 7, wherein the therapeutic agent is an antibiotic, an analgesic, or an anesthetic.

9. The catheter device of claim 1, wherein the lumen is configured to administer a therapeutic agent to the intervertebral disc.

10. The catheter device of claim 1, wherein the tubular body comprises two lumens.

* * * * *

UNITED STATES PATENT AND TRADEMARK OFFICE
CERTIFICATE OF CORRECTION

| | | |
|---|---|---|
| PATENT NO. | : 8,777,870 B2 | Page 1 of 1 |
| APPLICATION NO. | : 12/120846 | |
| DATED | : July 15, 2014 | |
| INVENTOR(S) | : Malek | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1054 days.

Signed and Sealed this

Thirteenth Day of October, 2015

Michelle K. Lee
*Director of the United States Patent and Trademark Office*